(12) United States Patent
McKenna et al.

(10) Patent No.: US 11,497,547 B2
(45) Date of Patent: Nov. 15, 2022

(54) JAW CLOSURE DETECTION SYSTEM

(71) Applicant: COVIDIEN LP, Mansfield, MA (US)

(72) Inventors: Nicole McKenna, Boulder, CO (US); Robert H. Wham, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 898 days.

(21) Appl. No.: 16/372,057

(22) Filed: Apr. 1, 2019

(65) Prior Publication Data

US 2019/0223942 A1  Jul. 25, 2019

Related U.S. Application Data

(60) Division of application No. 15/299,514, filed on Oct. 21, 2016, now Pat. No. 10,245,104, which is a
(Continued)

(51) Int. Cl.
*A61B 18/14* (2006.01)
*A61B 17/29* (2006.01)
(Continued)

(52) U.S. Cl.
CPC ...... *A61B 18/1447* (2013.01); *A61B 18/1442* (2013.01); *A61B 18/1445* (2013.01);
(Continued)

(58) Field of Classification Search
CPC ............ A61B 17/29; A61B 2017/2926; A61B 2018/0063; A61B 18/1442;
(Continued)

(56) References Cited

U.S. PATENT DOCUMENTS

D249,549 S   9/1978 Pike
D263,020 S   2/1982 Rau, III
(Continued)

FOREIGN PATENT DOCUMENTS

CN  201299462 Y   9/2009
DE    2415263 A1  10/1975
(Continued)

OTHER PUBLICATIONS

Johnson et al. "Evaluation of the LigaSure Vessel Sealing System in Hemorrhoidectormy" American College of Surgeons (ACS) Clinicla Congress Poster (2000).
(Continued)

*Primary Examiner* — Ronald Hupczey, Jr.
*Assistant Examiner* — Bradford C. Blaise
(74) *Attorney, Agent, or Firm* — Carter, DeLuca & Farrell LLP

(57) ABSTRACT

A jaw angle detection system for an end effector assembly includes a first electrical contact that connects to a first jaw member and connects to a generator. A sensor connects to a second jaw member (or an actuator) and connects to the generator, and configured to move relative to the first electrical contact upon movement of the second jaw member (or the actuator) when the first and second jaw members are moved to close about tissue disposed therebetween. Information relating to the position of the sensor relative to the first electrical contact is relayed back to the generator to determine an angle between the first and second jaw members.

15 Claims, 4 Drawing Sheets

Related U.S. Application Data continuation of application No. 14/295,757, filed on Jun. 4, 2014, now Pat. No. 9,474,570, which is a division of application No. 13/736,650, filed on Jan. 8, 2013, now Pat. No. 8,764,749, which is a division of application No. 12/419,735, filed on Apr. 7, 2009, now Pat. No. 8,357,158.

(60) Provisional application No. 61/046,882, filed on Apr. 22, 2008.

(51) Int. Cl.
    *A61B 18/00* (2006.01)
    *A61B 90/00* (2016.01)

(52) U.S. Cl.
    CPC ....... *A61B 17/29* (2013.01); *A61B 2017/2926* (2013.01); *A61B 2018/0063* (2013.01); *A61B 2090/067* (2016.02)

(58) Field of Classification Search
    CPC ............ A61B 18/1445; A61B 18/1447; A61B 2018/1452; A61B 34/30; A61B 34/32; A61B 34/35; A61B 34/37; A61B 2034/301; A61B 2034/302; A61B 2034/303; A61B 2034/304; A61B 2034/305; A61B 2034/306; A61B 2090/067
    See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 4,939,445 A | 7/1990 | Meline et al. |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,558,671 A | 9/1996 | Yates |
| D384,413 S | 9/1997 | Zlock et al. |
| 5,776,130 A | 7/1998 | Buysse et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| 6,004,335 A | 12/1999 | Vaitekunas et al. |
| 6,024,741 A | 2/2000 | Williamson, IV et al. |
| D424,694 S | 5/2000 | Tetzlaff et al. |
| D425,201 S | 5/2000 | Tetzlaff et al. |
| 6,066,139 A | 5/2000 | Ryan et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,887,536 B2 | 2/2011 | Johnson et al. |
| 8,016,827 B2 | 9/2011 | Chojin |
| D649,249 S | 11/2011 | Guerra |
| D649,643 S | 11/2011 | Allen, IV et al. |
| 8,112,871 B2 | 2/2012 | Brandt et al. |
| 8,114,122 B2 | 2/2012 | Nau, Jr. |
| 8,133,254 B2 | 3/2012 | Dumbauld et al. |
| 8,142,473 B2 | 3/2012 | Cunningham |
| 8,162,965 B2 | 4/2012 | Reschke et al. |
| 8,162,973 B2 | 4/2012 | Cunningham |
| D661,394 S | 6/2012 | Romero et al. |
| 8,197,479 B2 | 6/2012 | Olson et al. |
| 8,226,650 B2 | 7/2012 | Kerr |
| 8,251,994 B2 | 8/2012 | McKenna et al. |
| 8,257,387 B2 | 9/2012 | Cunningham |
| 8,266,783 B2 | 9/2012 | Brandt et al. |
| 8,277,446 B2 | 10/2012 | Heard |
| 8,282,634 B2 | 10/2012 | Cunningham et al. |
| 8,287,536 B2 | 10/2012 | Mueller et al. |
| 8,292,886 B2 | 10/2012 | Kerr et al. |
| 8,303,582 B2 | 11/2012 | Cunningham |
| 8,317,787 B2 | 11/2012 | Hanna |
| 8,323,310 B2 | 12/2012 | Kingsley |
| 8,328,803 B2 | 12/2012 | Regadas |
| 8,343,150 B2 | 1/2013 | Artale |
| 8,343,151 B2 | 1/2013 | Siebrecht et al. |
| 8,357,158 B2 | 1/2013 | McKenna et al. |
| 8,357,159 B2 | 1/2013 | Romero |
| 8,388,647 B2 | 3/2013 | Nau, Jr. et al. |
| 8,430,876 B2 | 4/2013 | Kappus et al. |
| 8,439,911 B2 | 5/2013 | Mueller |
| 8,469,956 B2 | 6/2013 | McKenna et al. |
| 8,469,957 B2 | 6/2013 | Roy |
| 8,486,107 B2 | 7/2013 | Hinton |
| 8,512,371 B2 | 8/2013 | Kerr et al. |
| 8,535,312 B2 | 9/2013 | Horner |
| 8,568,412 B2 | 10/2013 | Brandt et al. |
| 8,574,230 B2 | 11/2013 | Romero |
| 8,591,511 B2 | 11/2013 | Romero |
| 8,623,017 B2 | 1/2014 | Moses et al. |
| 8,632,539 B2 | 1/2014 | Twomey et al. |
| 8,632,564 B2 | 1/2014 | Cunningham |
| 8,636,761 B2 | 1/2014 | Cunningham et al. |
| 8,679,115 B2 | 3/2014 | Reschke |
| 8,679,140 B2 | 3/2014 | Butcher |
| RE44,834 E | 4/2014 | Dumbauld et al. |
| 8,747,434 B2 | 6/2014 | Larson et al. |
| 8,752,264 B2 | 6/2014 | Ackley et al. |
| 8,764,749 B2 | 7/2014 | McKenna et al. |
| 8,784,417 B2 | 7/2014 | Hanna |
| 8,795,274 B2 | 8/2014 | Hanna |
| 8,864,753 B2 | 10/2014 | Nau, Jr. et al. |
| 8,887,373 B2 | 11/2014 | Brandt et al. |
| 8,920,461 B2 | 12/2014 | Unger et al. |
| 8,939,975 B2 | 1/2015 | Twomey et al. |
| 8,961,513 B2 | 2/2015 | Allen, IV et al. |
| 8,961,514 B2 | 2/2015 | Garrison |
| 8,968,298 B2 | 3/2015 | Twomey |

(56) References Cited

U.S. PATENT DOCUMENTS

| | | |
|---|---|---|
| 8,968,308 B2 | 3/2015 | Horner et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,313 B2 | 3/2015 | Larson |
| 8,968,314 B2 | 3/2015 | Allen, IV |
| 8,968,358 B2 | 3/2015 | Reschke |
| 8,968,360 B2 | 3/2015 | Garrison et al. |
| 9,011,435 B2 | 4/2015 | Brandt et al. |
| 9,011,436 B2 | 4/2015 | Garrison |
| 9,023,035 B2 | 5/2015 | Allen, IV et al. |
| 9,023,039 B2 | 5/2015 | Kerr |
| 9,034,009 B2 | 5/2015 | Twomey et al. |
| 9,039,691 B2 | 5/2015 | Moua et al. |
| 9,072,524 B2 | 7/2015 | Heard et al. |
| 9,113,882 B2 | 8/2015 | Twomey et al. |
| 9,113,889 B2 | 8/2015 | Reschke |
| 9,113,897 B2 | 8/2015 | Deborski et al. |
| 9,113,899 B2 | 8/2015 | Garrison et al. |
| 9,113,901 B2 | 8/2015 | Allen, IV et al. |
| 9,113,903 B2 | 8/2015 | Unger |
| 9,113,904 B2 | 8/2015 | Kerr et al. |
| 9,161,769 B2 | 10/2015 | Stoddard et al. |
| 9,161,812 B2 | 10/2015 | Kerr |
| 9,168,052 B2 | 10/2015 | Garrison et al. |
| 9,192,421 B2 | 11/2015 | Garrison |
| 9,192,430 B2 | 11/2015 | Rachlin et al. |
| 9,192,432 B2 | 11/2015 | Larson et al. |
| 9,259,268 B2 | 2/2016 | Behnke, II et al. |
| 9,265,565 B2 | 2/2016 | Kerr |
| 9,265,569 B2 | 2/2016 | Hart et al. |
| 9,265,573 B2 | 2/2016 | Kerr |
| 9,314,295 B2 | 4/2016 | Garrison |
| 9,375,254 B2 | 6/2016 | Heard |
| 9,375,258 B2 | 6/2016 | Kendrick |
| 9,375,282 B2 | 6/2016 | Nau, Jr. et al. |
| 9,474,570 B2 | 10/2016 | McKenna et al. |
| 9,492,221 B2 | 11/2016 | Garrison |
| 9,545,262 B2 | 1/2017 | Kerr et al. |
| 9,603,652 B2 | 3/2017 | Carlton et al. |
| 9,693,816 B2 | 7/2017 | Orszulak |
| 9,713,493 B2 | 7/2017 | Waaler et al. |
| 9,820,765 B2 | 11/2017 | Allen, IV et al. |
| 9,820,806 B2 | 11/2017 | Lee et al. |
| 9,918,771 B2 | 3/2018 | Regadas |
| 10,245,104 B2 | 4/2019 | McKenna et al. |
| 2003/0199869 A1 | 10/2003 | Johnson et al. |
| 2004/0064151 A1 | 4/2004 | Mollenauer |
| 2005/0131390 A1 | 6/2005 | Heinrich et al. |
| 2005/0154387 A1 | 7/2005 | Moses et al. |
| 2006/0047278 A1 | 3/2006 | Christian et al. |
| 2006/0084973 A1 | 4/2006 | Hushka |
| 2007/0106297 A1 | 5/2007 | Dumbauld et al. |
| 2007/0179512 A1 | 8/2007 | Olsen et al. |
| 2008/0009860 A1 | 1/2008 | Odom |
| 2008/0033428 A1 | 2/2008 | Artale et al. |
| 2008/0039836 A1 | 2/2008 | Odom et al. |
| 2008/0251568 A1 | 10/2008 | Zemlok et al. |
| 2010/0042143 A1 | 2/2010 | Cunningham |
| 2010/0057081 A1 | 3/2010 | Hanna |
| 2010/0063500 A1 | 3/2010 | Muszala |
| 2010/0069903 A1 | 3/2010 | Allen, IV et al. |
| 2010/0069953 A1 | 3/2010 | Cunningham et al. |
| 2010/0076430 A1 | 3/2010 | Romero |
| 2010/0249769 A1 | 9/2010 | Nau, Jr. et al. |
| 2011/0054468 A1 | 3/2011 | Dycus |
| 2011/0054471 A1 | 3/2011 | Gerhardt et al. |
| 2011/0060335 A1 | 3/2011 | Harper et al. |
| 2011/0071523 A1 | 3/2011 | Dickhans |
| 2013/0274736 A1 | 10/2013 | Garrison |
| 2013/0304066 A1 | 11/2013 | Kerr et al. |

FOREIGN PATENT DOCUMENTS

| | | |
|---|---|---|
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19932962 A1 | 1/2001 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102004026179 B4 | 1/2009 |
| DE | 102008018406 B3 | 7/2009 |
| EP | 1159926 A2 | 3/2003 |
| EP | 1472984 A1 | 11/2004 |
| EP | 1707143 A1 | 10/2006 |
| JP | 61501068 A | 5/1986 |
| JP | H055106 A | 1/1993 |
| JP | H0540112 A | 2/1993 |
| JP | H06502328 A | 3/1994 |
| JP | H06121797 A | 5/1994 |
| JP | H06285078 A | 10/1994 |
| JP | H06343644 A | 12/1994 |
| JP | H06511401 A | 12/1994 |
| JP | H07265328 A | 10/1995 |
| JP | H0856955 A | 3/1996 |
| JP | H08252263 A | 10/1996 |
| JP | H08289895 A | 11/1996 |
| JP | H08317934 A | 12/1996 |
| JP | H08317936 A | 12/1996 |
| JP | H09538 A | 1/1997 |
| JP | H0910223 A | 1/1997 |
| JP | H09122138 A | 5/1997 |
| JP | H10195 A | 1/1998 |
| JP | H1024051 A | 1/1998 |
| JP | H10155798 A | 6/1998 |
| JP | H1147150 A | 2/1999 |
| JP | H1170124 A | 3/1999 |
| JP | H11169381 A | 6/1999 |
| JP | H11192238 A | 7/1999 |
| JP | H11244298 A | 9/1999 |
| JP | 2000102545 A | 4/2000 |
| JP | 2000342599 A | 12/2000 |
| JP | 2000350732 A | 12/2000 |
| JP | 2001003400 A | 1/2001 |
| JP | 2001008944 | 1/2001 |
| JP | 2001029356 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| JP | 6030945 B2 | 11/2016 |
| SU | 401367 A1 | 10/1973 |
| WO | 0036986 A1 | 6/2000 |

(56) References Cited

FOREIGN PATENT DOCUMENTS

| WO | 0059392 A1 | 10/2000 |
|---|---|---|
| WO | 0115614 A1 | 3/2001 |
| WO | 0154604 A1 | 8/2001 |
| WO | 0245589 A2 | 6/2002 |
| WO | 03090630 A2 | 11/2003 |
| WO | 2006021269 A1 | 3/2006 |
| WO | 2005110264 A2 | 4/2006 |
| WO | 2008040483 A1 | 4/2008 |

OTHER PUBLICATIONS

Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: a Case Report" Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: a New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
U.S. Appl. No. 12/336,970, filed Dec. 17, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 12/336,970, filed Dec. 17, 2008, Paul R. Sremeich.
U.S. Appl. No. 13/731,674, filed Dec. 31, 2012, Siebrecht.
Michael Choti, "Abdominoperineal Resection with the LigaSure Vessel Sealing System and LigaSure Atlas 20 cm Open Instrument" Innovations That Work, Jun. 2003.

(56) References Cited

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al., "Comparison of Healing Process Following Ligation with Sutures and Bipolar Vessel Sealing" Surgical Technology International (2001).
"Electrosurgery: a Historical Overview" Innovations in Electrosurgery; Sales-Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005; LNCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
U.S. Appl. No. 09/591,328, filed Jun. 9, 2000, Thomas P. Ryan.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report-extended-EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended-EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.

JAW CLOSURE DETECTION SYSTEM

CROSS REFERENCE TO RELATED APPLICATIONS

This application is a divisional of U.S. patent application Ser. No. 15/299,514, filed Oct. 21, 2016, now U.S. Pat. No. 10,245,104, which is a continuation of U.S. patent application Ser. No. 14/295,757, filed Jun. 4, 2014, now U.S. Pat. No. 9,474,570, which is a divisional of U.S. patent application Ser. No. 13/736,650, filed Jan. 8, 2013, now U.S. Pat. No. 8,764,749, which is a divisional of U.S. patent application Ser. No. 12/419,735, filed Apr. 7, 2009, now U.S. Pat. No. 8,357,158, which claims the benefit of the filing date of provisional U.S. Patent Application No. 61/046,882, filed Apr. 22, 2008, the entire contents of each of which are incorporated herein by reference.

INTRODUCTION

The present disclosure relates to a jaw closure detection system for performing electrosurgical procedures. More particularly, the present disclosure relates to a jaw sensing system that detects and/or confirms jaw closure about tissue and/or detects the relative angle of two opposing jaw members relative to one another when tissue is engaged therebetween.

BACKGROUND

Forceps utilize mechanical action to constrict, grasp, dissect and/or clamp tissue. Electrosurgical forceps utilize both mechanical clamping action and electrical energy to effect hemostasis by heating the tissue and blood vessels. By controlling the intensity, frequency and duration of the electrosurgical energy applied through the jaw members to the tissue, the surgeon can coagulate, cauterize and/or seal tissue.

In order to effect a proper seal with larger vessels or thick tissue, two predominant mechanical parameters must be accurately controlled: the pressure applied to the tissue; and the gap distance between the electrodes. As can be appreciated, both of these parameters are affected by the thickness of vessels or tissue. More particularly, accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal.

In some instances, in order to properly and effectively seal larger vessels or tissue, a greater closure force between opposing jaw members is required and accurate detection of jaw closure and in some cases the jaw closure angle is important to assure a consistent and reliable seal. This presents a design challenge for manufacturers because the jaw members are typically affixed with pins which are positioned to have small moment arms with respect to the pivot of each jaw member and it is often difficult to asses accurate jaw closure. Further, many of these known instruments generally rely on clamping pressure alone to procure proper sealing thickness and are often not designed to take into account jaw closure variables relating to gap tolerances and/or parallelism and flatness requirements which are parameters which, if properly controlled, can assure a consistent and effective tissue seal. Confirmation that the jaw members are both closed about tissue and oriented at a correct angle are important factors which, when properly controlled, assure a consistent and reliable tissue seal.

SUMMARY

The present disclosure relates to a jaw closure mechanism or jaw angle detector for an end effector assembly of a forceps and includes a first electrical contact that connects to a first jaw member and connects to a generator (or a controller). A sensor is included that connects to a second jaw member (or an actuator) and connects to the generator/controller. The sensor is configured to move relative to the first electrical contact upon movement of the second jaw member (or the actuator) when the first and second jaw members are moved to close about tissue disposed therebetween. Information relating to the position of the sensor relative to the first electrical contact is relayed back to the generator/controller to determine an angle between the first and second jaw members. This information is conveyed to the user by a monitor or other type of visual or audible indicator. The relative position of the first electrical contact relative to the sensor may be represented in binary code.

In embodiments, the sensor includes a variable resistor, a series of resistors or a voltage divider network (potentiometer) that relays information back to the generator (or controller). In yet another embodiment, the sensor includes a variable capacitor that may include first and second conductive rings, the first conductive ring being fixed relative to the second conductive ring.

In another embodiment, the sensor includes a second electrical contact that is positioned to conduct a signal back to the generator/controller when the second electrical contact electrically connects to the first electrically contact upon the jaw members closing about tissue past a particular angle, e.g., a threshold angle. The threshold angle being an angle wherein the jaw members are closed about tissue to assure a consistent and reliable seal.

The present disclosure also relates to a jaw angle detector having first and second jaw members and first and second conductors (e.g., conductive rings) adapted to connect to a capacitive sensing circuit of an electrical generator. The first conductor is fixed relative to the second conductor and the second conductor is moveable relative to the first conductor upon movement of the jaw members from a first spaced position relative to one another to a second position closer to one another. Information relating to the position of the second conductor relative to the first conductor is relayed back to the capacitive sensing circuit to determine an angle between the first and second jaw members. In embodiments, the second conductor is attached to a drive rod of an endoscopic electrosurgical forceps or a movable jaw member of a unilateral endoscopic electrosurgical forceps.

The present disclosure also relates to a jaw angle detector that includes first and second jaw members each having proximally extending flanges adapted to connect to an electrosurgical energy source for conducting energy through tissue held between jaw members. A conductor is disposed on the proximal flange of the first jaw member and a variable resistor (e.g., series of resistors, voltage divider network, etc.) is disposed on the proximal flange of the second jaw member in opposing relation to the conductor. The first conductor and the variable resistor are adapted to relay a signal to a sensing circuit of the electrosurgical generator. The movement of the jaw members from an open spaced apart position to a closed position causes the conductor to move across the variable resistor and vary the signal relayed back to the sensing circuit, which, in turn, determines an angle between the first and second jaw members. In embodiments, the variable resistor is disposed in a port defined in the second jaw member, the port being configured to mechanically receive the conductor therein.

BRIEF DESCRIPTION OF THE DRAWINGS

Various embodiments of the present disclosure are described herein with reference to the drawings wherein.

DETAILED DESCRIPTION

Figure 1A:
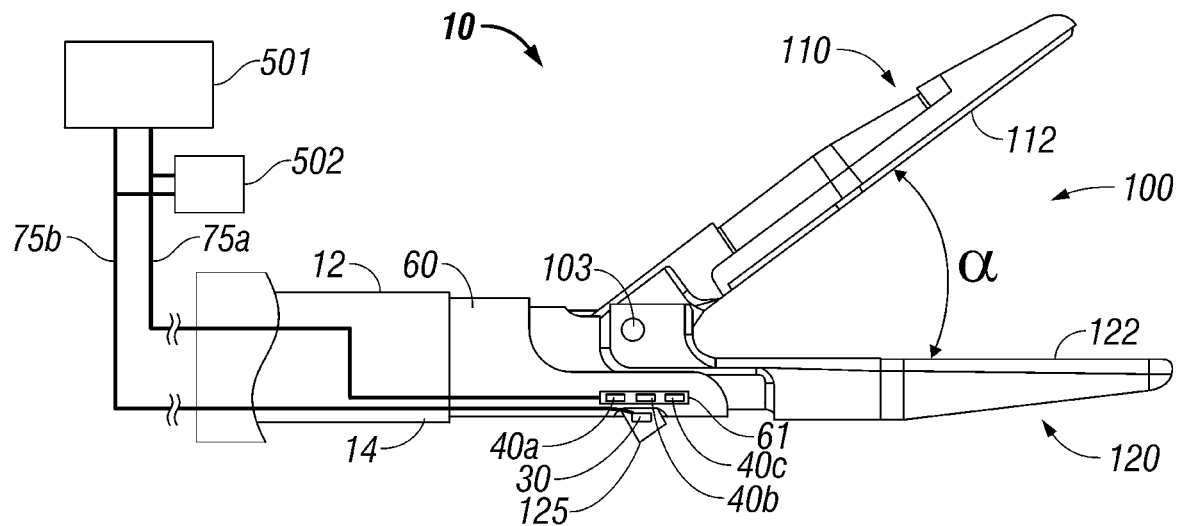
FIG. 1A is a side view of unilateral laparoscopic bipolar forceps configured to support one embodiment of a jaw closure detection system according to the present disclosure.

Referring to FIGS. 1A-6, various embodiments of a jaw closure detector or sensing mechanism are disclosed in accordance with the present disclosure. A laparoscopic, an endoscopic, or an open instrument may be utilized for supporting the jaw closure detector assembly; however, different electrical and mechanical connections and considerations apply to each particular type of instrument. In the drawings and in the description that follows, the term "proximal", as is traditional, will refer to the end of the forceps that is closer to the user, while the term "distal" will refer to the end of the forceps that is further from the user.

FIG. 1A shows a unilateral laparoscopic vessel sealing forceps 10 that is configured to support an electrode sealing assembly 100. Forceps 10 typically includes various conventional features (e.g., housing, a handle assembly, a rotating assembly, a trigger assembly (all not shown)) that enable the forceps 10 and the end effector assembly 100 to mutually cooperate to grasp, seal and, if warranted, divide tissue. The forceps 10 includes a shaft 12 that has a distal end 14 dimensioned to mechanically engage the end effector assembly 100 and a proximal end (not shown) that mechanically engages the housing (not shown). Details relating to the inter-cooperative relationships of the various components of forceps 10 are disclosed in commonly-owned U.S. Pat. No. 7,150,749, the entire contents of which is incorporated by reference herein.

Forceps 10 also includes a plug (not shown) that connects the forceps 10 to a source of electrosurgical energy, e.g., an electrosurgical generator 501, via one or more electrical cables (not shown). Other electrical connections (not shown) are positioned through the shaft 12 and end effector assembly 100 to supply bipolar electrical energy to opposing sealing surfaces 112 and 122 of jaw members 110 and 120, respectively. The jaw members 110 and 120 move in response to movement of an actuator or handle (not shown) from an open position wherein the electrically conductive sealing surfaces 112 and 122 are disposed in spaced relation relative to one another, to a clamping or closed position wherein the electrically conductive sealing surfaces 112 and 122 cooperate to grasp tissue 401 (See FIG. 2) therebetween. Again, details relating to the inter-cooperative relationships of the inner-working components of the actuator or handle of the forceps 10 are disclosed in commonly-owned U.S. Pat. No. 7,150,749, incorporated by reference above. When the electrically conductive sealing surfaces 112 and 122 of the jaw members 110 and 120 are fully compressed about the tissue, the forceps 10 is now ready for selective application of electrosurgical energy.

As mentioned above, FIG. 1A shows a bipolar forceps 10 that includes a unilateral end effector assembly 100 having one stationary or fixed jaw member 120 mounted in fixed relation to the shaft 12 and pivoting jaw member 110 mounted about a pivot pin 103 attached to the stationary jaw member 120. A reciprocating sleeve 60 is slidingly disposed within the shaft 12 and is remotely operable by the drive actuator (not shown). The pivoting jaw member 110 includes a detent or protrusion 125 that extends from jaw member 110 through an aperture defined within the reciprocating sleeve 60. The pivoting jaw member 110 is actuated by sliding the sleeve 60 axially within the shaft 12 such that a distal end of the aperture abuts against the detent 125 on the pivoting jaw member 110. Pulling the sleeve 60 proximally closes the jaw members 110 and 120 about tissue grasped therebetween and pushing the sleeve 60 distally opens the jaw members 110 and 120 for grasping purposes.

In one embodiment, one of the jaw members, e.g., jaw members 110, includes a sensor 30 disposed on detent 125. Reciprocating sleeve 60 includes one or more corresponding sensors 40a-40c disposed on a distal end 61 thereof. The sensors 30 and 40a-40c are electrically coupled to a feedback circuit associated with the generator 501 or an independent controller 502 via leads 75b and 75a, respectively, which determines the position of sensor 30 relative to sensors 40a-40c, respectively, and associates the relative position with a jaw angle "α" between jaw members 110 and 120. The sensors 30 and 40a-40c may be magnetic, resistive, capacitive, optical or any other suitable type of sensor. In use, as the user actuates the drive sleeve 60 proximally to close the jaw members 110 and 120 relative to one another, sensor 30, in turn, moves relative to sensors 40c-40a. The feedback loop calculates the angle "α" of the jaw members 110 and 120 and provides the information back to the user.

The sensors 30 and 40a-40c may also be configured to provide additional feedback to the user relating to tissue thickness (based on relative resistance to closure), speed of jaw closure and if the jaw members 110 and 120 are closed appropriately about tissue for application of electrosurgical energy. Moreover, jaw closure angle "α" may be used to determine a "re-grasp" condition during sealing due to insufficient jaw closure or may be used to determine the overall adequacy of the seal either prior to, during, or after activation. In another embodiment, the jaw closure angle "α" may be used modify the energy delivery from the generator 501 to enhance the sealing process.

Figure 2:
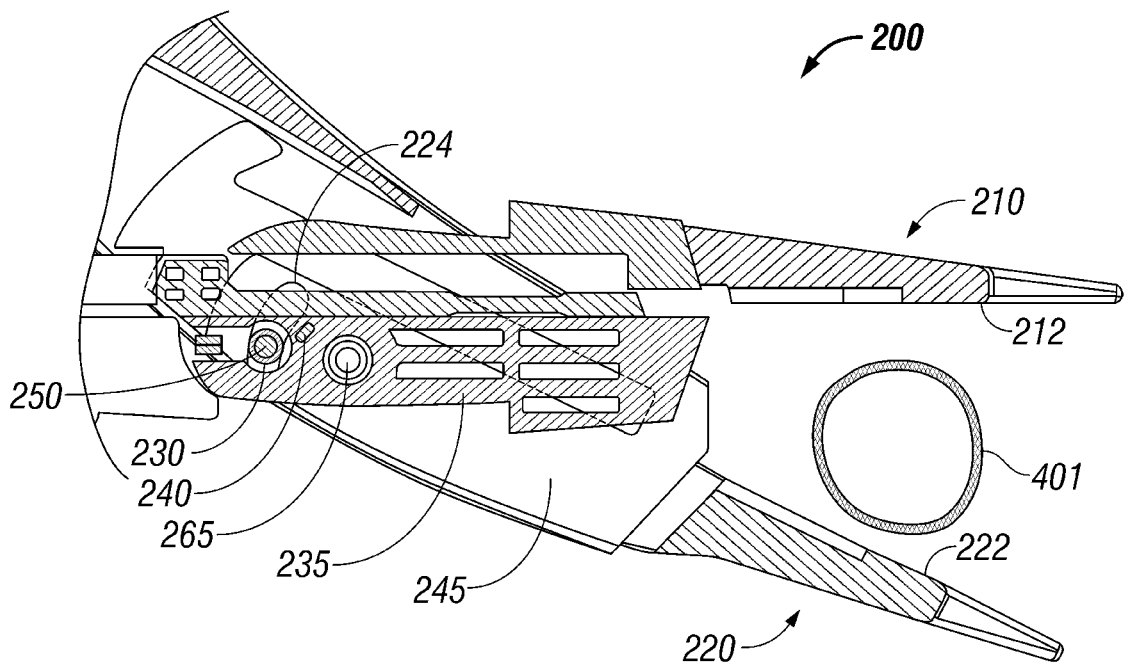
FIG. 2 is an enlarged, side view of an end effector assembly of an open bipolar forceps configured to support one embodiment of a jaw closure detection system according to the present disclosure.

In another embodiment, a single electrical contact 240 may act as a sensor to determine jaw closure and provide information to the generator 501 regarding the jaw angle "α". For example, FIG. 2 shows another forceps design 200 that includes two opposing jaw members 210 and 220 movable relative to one another about a pivot 265 to engage tissue. Jaw members 210 and 220 each include an electrically conductive surface 212 and 222, respectively, disposed thereon that connects to generator 501 for selectively conducting bipolar energy through tissue.

Jaw member 220 also includes a proximal portion or base 245 having guide slot 224 defined therein that allows a terminal connector 250 or so-called "POGO" pin to ride therein upon movement of the jaw members 210 and 220 from the open to closed positions. A corresponding base 235 of jaw member 210 includes a sensor or contact 240 disposed proximate slot 224 that electrically connects to the generator 501 or independent controller 502. As explained above, the sensor 240 may be configured to provide information back to the generator via one or more feedback loops relating to the angle "α" of the jaw members 210 and 220 relative to one another.

Sensor 240 may also be configured to provide additional information back to the generator 501 as explained above. In one embodiment, the sensor 240 may act as a safety mechanism wherein the electrical contact 240 simply determines if the two opposing jaw members 210 and 220 are moved close enough together (e.g., have moved past a threshold angle) for application of electrical energy. In this manner, when the jaw members 210 and 220 are closed to an angle less than desired or less than appropriate to commence sealing, the sensor 240 does not electrically connect to terminal connector 250 to send a signal back to the generator 501 to allow activation. For example, when the jaw members 210 and 220 are opened at an angle not appropriate to seal vessels or tissue, the sensor 240 may be positioned opposite (or relative to) a non-conductive material and, as a result, does not conduct a signal back to the generator 501. Conversely, when the jaw members 210 and 220 are closed past a threshold angle, the sensor 240 is positioned opposite (or relative to) terminal connector 250 and conducts a signal back to generator 501 to allow activation.

Figure 1B:
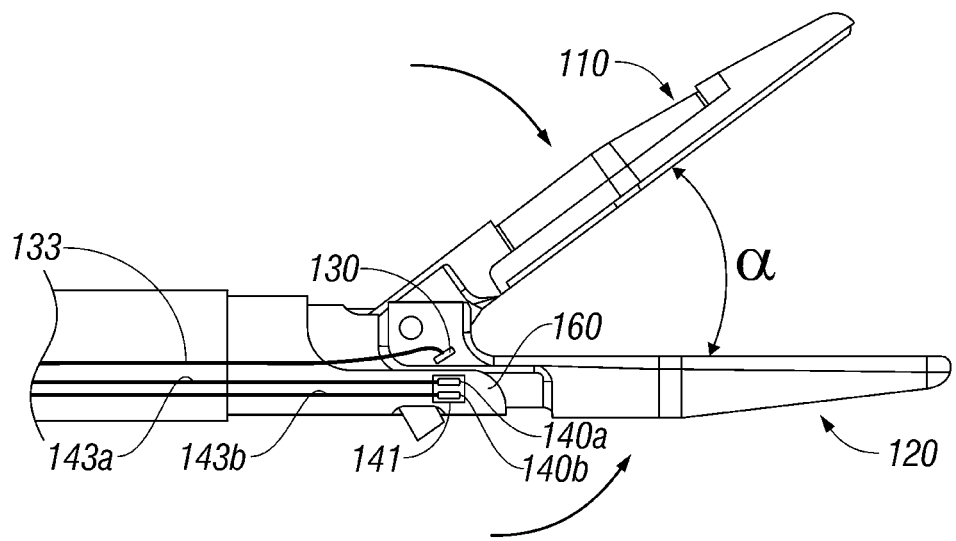
FIG. 1B is an enlarged, side view of an end effector assembly of an open bipolar forceps configured to support another embodiment of a jaw closure detection system according to the present disclosure.

In some embodiments, a series of sensors e.g., sensors 140a and 140b, may be employed along or on a distal end of drive sleeve 160 such that the relative angle "α" between the jaw members 110 and 120 may be divided into discreet units for finer resolution (See FIG. 1B). For example, in the instance where two sensors 140a and 140b are utilized to determine the relative angle between jaw members 110 and 120, information relating to the state of conductivity of each electrical connection between the respective sensors 140a and 140b and connector 130 can be communicated back to the generator 501 via leads 133, 143a and 143b, respectively, in binary format, e.g., "00" (no contact with either sensor 143a or 143b); "01" (contact with first sensor 143a); "11" (contact with both sensors 143a and 143b); and "10" (contact with second sensor 143b).

Figure 3:
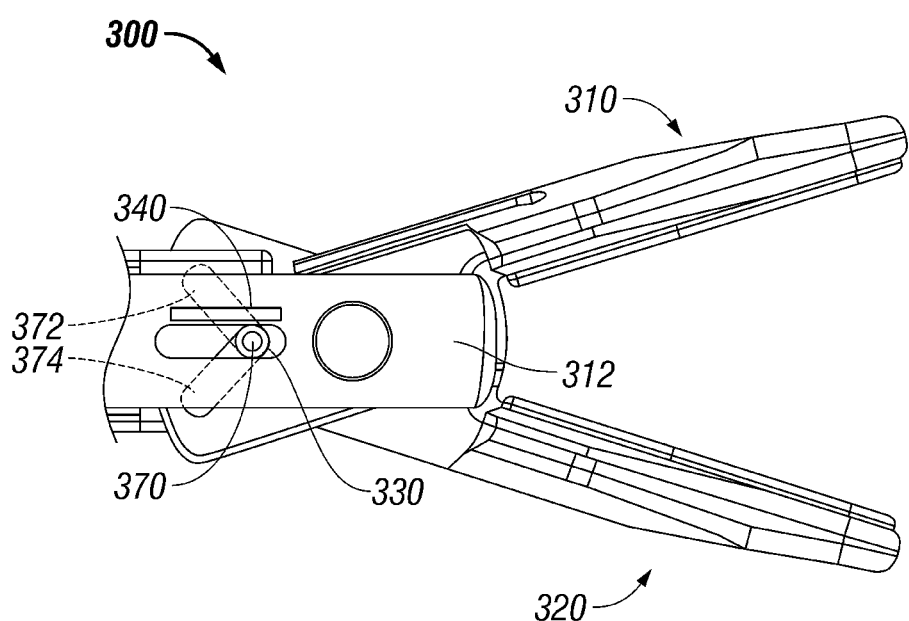
FIG. 3 is a side view of a bilateral endoscopic bipolar forceps configured to support another embodiment of a jaw closure detection system according to the present disclosure including a variable resistor.

FIG. 3 shows yet another forceps 300 that utilizes a variable resistor 340, e.g., a voltage divider network ("VDN"), to determine jaw angle "α". VDN 340 may be a film-type potentiometer that forms a switch closure. For the purposes herein, the term "voltage divider network" relates to any suitable form of resistive, capacitive or inductive switch closure (or the like) that determines the output voltage across a voltage source (e.g., one of two impedances) connected in series. A "voltage divider" as used herein relates to a number of resistors connected in series that are provided with taps at certain points to make available a fixed or variable fraction of the applied voltage.

In this instance, actuating pin 330 would act as a contact across the VDN 340 such that, as the actuating pin 330 is translated within a slot 345 within shaft 312 and respective cam slots 374 and 372 in jaw members 310 and 320, the actuating pin 330 would move relative to the VDN 340, thereby varying the intensity of the signal relayed back to the generator 501 which, in turn, may be utilized to determine jaw angle "α". Additional wiring (not shown) may be required to accomplish this purpose, but a finer resolution of jaw angle "α" may be determined.

Figure 4A:
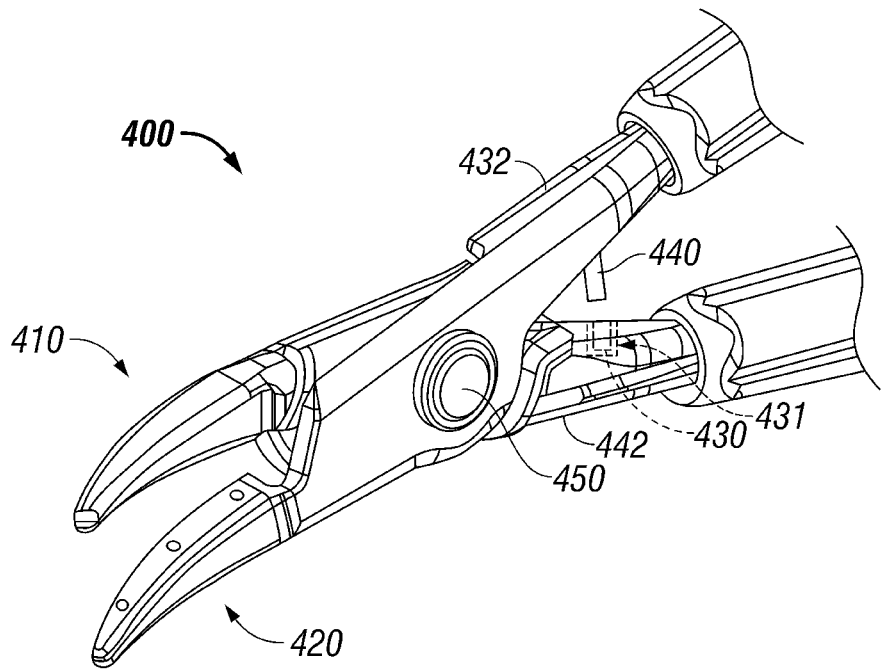
FIG. 4A is a front, perspective view of an end effector assembly of an open forceps showing a jaw closure detection system in a first orientation prior to grasping tissue.
Figure 4B:
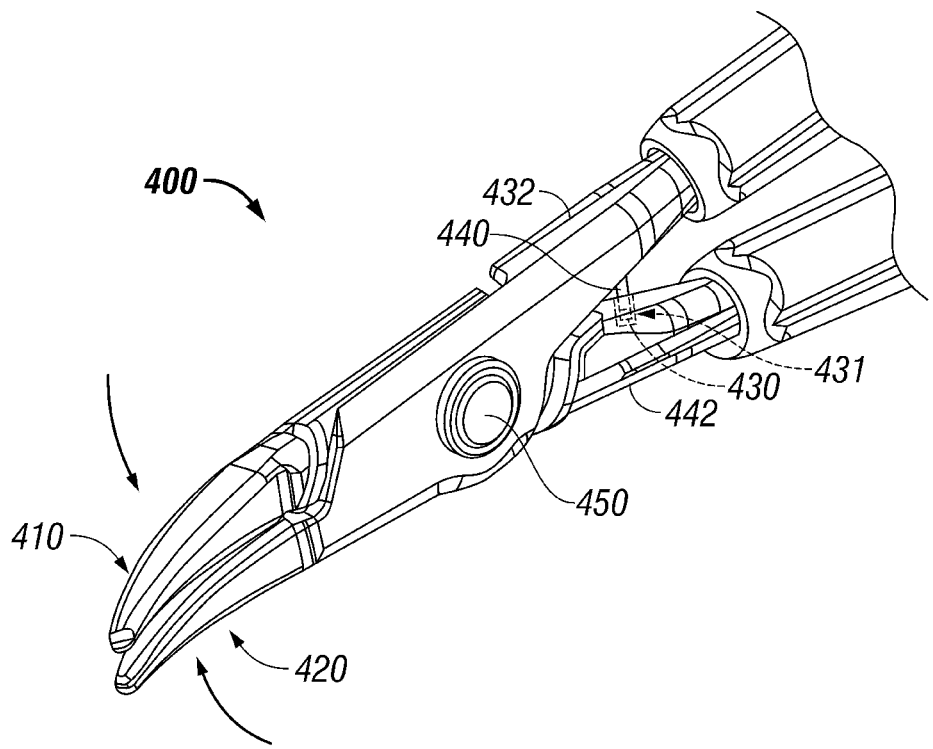
FIG. 4B is a front, perspective view of the end effector assembly of FIG. 4A showing the jaw closure detection system in a second orientation with the jaw members closed.

FIGS. 4A and 4B show another embodiment of an open forceps 400 having a similar style sensor arrangement for determining jaw angle "α". More particularly, forceps 400 includes two opposing jaw members 410 and 420 that are movable relative to one another about a pivot 450. Each jaw member 410 and 420 includes a flange 442 and 432 that extends proximally therefrom. Flange 432 includes a contact 440 that is mechanically received within a complementary interface 431 disposed on flange 442 that houses VDN 430. During movement of the jaw members 410 and 420 from the open position to the closed position, contact 440 moves from a spaced position relative to interface 431 (as shown in FIG. 4A) to a series of subsequent positions within interface 431 as the contact 440 moves across the VDN (or series of resistors), thereby varying the intensity of the signal relayed back to the generator 501 for determining jaw angle "α".

Figure 5:
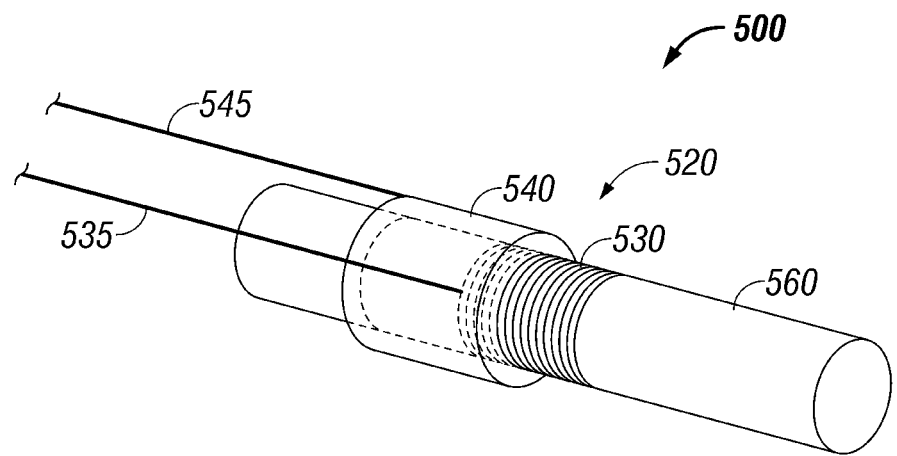
FIG. 5 is a schematic view of a drive actuator of an endoscopic forceps configured to support another embodiment of a jaw closure detection system according to the present disclosure including a variable capacitor.

FIG. 5 shows another embodiment of a forceps 500 wherein a drive actuator 560 has been modified to include a variable capacitor 520 to determine the jaw angle "α" between two opposing jaw members, e.g., jaw members 110 and 120. More particularly, variable capacitor 520 includes a fixed conductor, e.g., a conductive ring 540 disposed on a forceps housing (not shown) or jaw member 110 and 120 that encapsulates a second conductor, e.g., a conductive ring 530, disposed on the drive actuator 560. Movement of the drive actuator 560 moves the conductive ring 530 relative to the conductive ring 540. A dielectric insulator (not shown) may be placed between the two rings 530 and 540 (e.g., air or insulating lubricant).

As the drive actuator 560 moves to close the jaw members 110 and 120, the conductive rings 530 move relative to the fixed conductive ring 540 thereby changing the capacitance between the two conductive rings 530 and 540 based on a capacitive sensing circuit 600 described below with respect to FIG. 6. The change in capacitance can be detected and transmitted to the generator 501 or controller 502 to determine the jaw closure angle "α" between the two jaw members 110 and 120. In one embodiment, the conductive rings 530 and 540 may both be movable relative to one another to accomplish a similar purpose.

Figure 6:
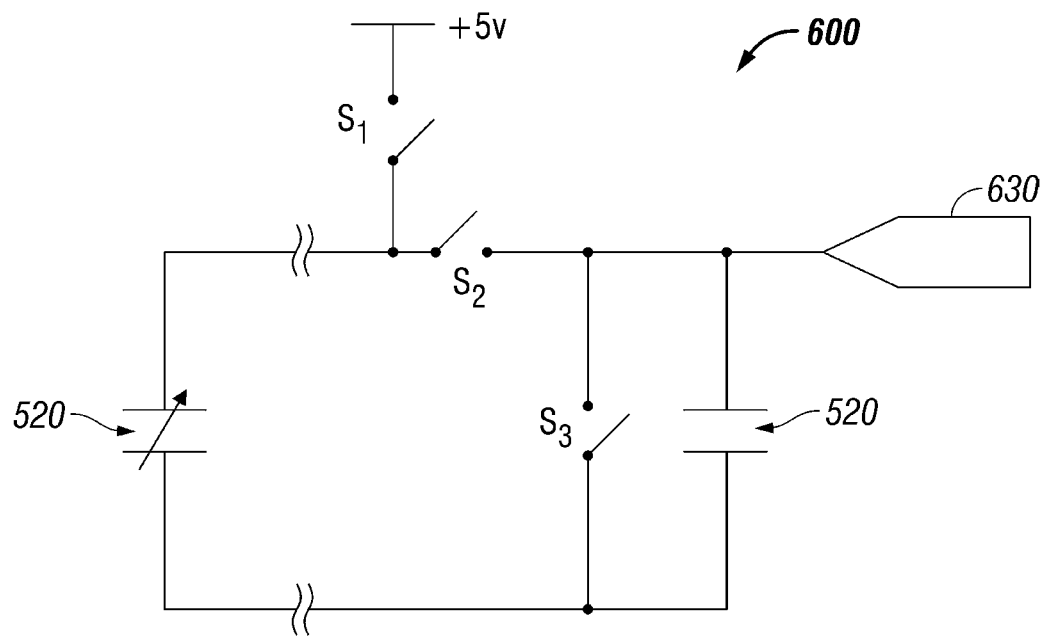
FIG. 6 is a schematic circuit diagram of a capacitive sensing circuit for use with the variable capacitor of FIG. 5.

FIG. 6 shows one example of a variable capacitance circuit 600 for use with the embodiment described with respect to FIG. 5. As mentioned above, the conductive rings 540 and 530 form a variable capacitor 520 that transmits a signal back to the generator 501 and circuit 600. The connection of the variable capacitor 520 to the voltage source (labeled +5 v) causes the variable capacitor 520 to charge when S2 is open, S3 is open and S1 is shut. After a predetermined amount of time, S1 opens and S2 shuts. This causes the charge stored on the variable capacitor 520 to be transferred to the charge capacitor 620. S2 then opens and the process is repeated for a predetermined number of cycles. The resulting voltage on the charge capacitor 620 can then be read (in this case by an analog to digital converter 630). S3 is then closed and re-opened to discharge the charge capacitor 620. The entire cycle is then repeated at a desired read rate. The read voltage is proportional to the capacitance of the variable capacitor 520 which, in turn, relates to the jaw angle "α" between jaw members, e.g., jaw members 110 and 120.

From the foregoing and with reference to the various figure drawings, those skilled in the art will appreciate that certain modifications can also be made to the present disclosure without departing from the scope of the same. For example, one or more stop members may be disposed adjacent to or disposed on one or both electrically conductive sealing surfaces of the jaw members to regulate the gap distance between conductive surfaces. The distance the stop members extend from the electrically conductive surfaces may effect the jaw angle "α" between jaw members. The generator may have to be programmed (automatically or manually) to account for this feature when determining the overall jaw angle "α" and any type of threshold angle as mentioned above. Moreover, the tissue thickness may also effect the jaw angle "α". Again the generator may have to be programmed (automatically or manually) to compensate for these various tissue types.

One or more of the jaw closure detectors described herein may be configured to detect the change in the jaw closure angle "α" over a period of time during the sealing process. This information may also be relayed back to the generator for determining seal quality and overall success of the resulting seal.

In some embodiments, any of jaw closure detectors described herein may be coupled to a controller 502 that is electrically coupled to the generator 501 or, in some instances, independent from the generator 501. The controller 501 (if independent) may be configured to provide any or all of the features described herein with respect generator 501.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical system, comprising:
    a forceps including:
        a shaft having a proximal portion and a distal portion, the shaft including a variable resistor disposed on the distal portion thereof;
        an end effector operably coupled to the distal portion of the shaft and including:
            a first jaw member; and
            a second jaw member movably coupled to the first jaw member; and
        an actuator movable within and relative to the shaft to move the end effector between an open position and a closed position, the actuator including a contact that moves relative to the variable resistor upon movement of the actuator; and
    a controller in communication with the variable resistor and configured to determine an angle between the first and second jaw members based on a position of the contact relative to the variable resistor.

2. The surgical system according to claim 1, wherein each of the first and second jaw members defines a cam slot, the contact configured to move through the cam slots to move the end effector between the open and closed positions.

3. The surgical system according to claim 1, wherein the variable resistor is a voltage divider network.

4. The surgical system according to claim 1, wherein the actuator includes a reciprocating sleeve that defines an aperture therein, the first jaw member having a protrusion extending through the aperture such that axial movement of the sleeve relative to the second jaw member moves the end effector between the open and closed positions.

5. The surgical system according to claim 1, wherein the variable resistor comprises a series of resistors.

6. The surgical system according to claim 1, wherein movement of the contact relative to the variable resistor varies a signal communicated from the variable resistor to the controller.

7. A surgical device, comprising:
    a shaft having a variable resistor disposed thereon;
    an end effector disposed at a distal portion of the shaft and including a first jaw member movably coupled to a second jaw member;
    an actuator operably coupled to the end effector; and
    an actuating pin coupled to the actuator and configured, upon movement of the actuator, to:
        move within a cam slot defined by at least one of the first or second jaw members to move the end effector between an open position and a closed position; and
        move relative to the variable resistor for determining an angle between the first and second jaw members based on a position of the actuating pin relative to the variable resistor.

8. The surgical device according to claim 7, wherein the variable resistor is a voltage divider network.

9. The surgical device according to claim 7, wherein movement of the actuating pin relative to the variable resistor varies a signal generated by the variable resistor for determining the angle between the first and second jaw members.

10. The surgical device according to claim 7, wherein the variable resistor comprises a series of resistors.

11. A surgical device, comprising:
    a shaft having a variable resistor disposed thereon;
    an end effector disposed at a distal portion of the shaft and including a first jaw member movably coupled to a second jaw member; and
    an actuator operably coupled to the end effector via an actuating pin and configured to move the actuating pin relative to the variable resistor for determining an angle between the first and second jaw members based on a position of the actuating pin relative to the variable resistor.

12. The surgical device according to claim 11, wherein the actuator is configured to move the actuating pin within a cam slot defined by at least one of the first or second jaw members to move the end effector between an open position and a closed position.

13. The surgical device according to claim 11, wherein the variable resistor is a voltage divider network.

14. The surgical device according to claim 11, wherein movement of the actuating pin relative to the variable resistor varies a signal generated by the variable resistor for determining the angle between the first and second jaw members.

15. The surgical device according to claim 11, wherein the variable resistor comprises a series of resistors.

* * * * *